US006387949B1

(12) United States Patent
Delorme et al.

(10) Patent No.: US 6,387,949 B1
(45) Date of Patent: May 14, 2002

(54) SUBSTITUTED UREA COMPOUNDS USEFUL IN PAIN MANAGEMENT

(75) Inventors: Daniel Delorme, Quebec (CA); Vlad Gregor, San Diego, CA (US); Niklas Plobeck, Quebec (CA); Edward Roberts, Solothurn (CH); Eric Sun, San Diego, CA (US)

(73) Assignee: AstraZeneca Canada Inc., Ontario (CA)

( * ) Notice: Subject to any disclaimer, the term of this patent is extended or adjusted under 35 U.S.C. 154(b) by 0 days.

(21) Appl. No.: 09/555,580

(22) PCT Filed: Jun. 16, 1999

(86) PCT No.: PCT/SE99/01077

§ 371 Date: Jun. 1, 2000

§ 102(e) Date: Jun. 1, 2000

(87) PCT Pub. No.: WO99/67206

PCT Pub. Date: Dec. 29, 1999

(30) Foreign Application Priority Data

Jun. 22, 1998 (SE) .............................. 9802208

(51) Int. Cl.⁷ .............................. A61K 31/17
(52) U.S. Cl. .................... 514/482; 514/231.2; 514/248; 514/277; 514/426; 544/224; 544/106; 546/304; 548/557; 564/57; 564/435
(58) Field of Search .............................. 564/32, 47, 57, 564/58, 435; 544/106, 224; 548/557; 546/304; 514/228.8, 231.2, 248, 277, 408–426, 482

(56) References Cited

U.S. PATENT DOCUMENTS 4,634,713 A * 1/1987 Werner et al. .............. 514/392
5,849,732 A 12/1998 Suzuki et al. ............... 514/212

FOREIGN PATENT DOCUMENTS

EP  096 006   12/1983   ......... C07D/233/36
EP  790 240   8/1997    ......... C07D/213/40

OTHER PUBLICATIONS

Takemori, et al., "Selective Natrexone–Derived Opioid Receptor Antagonists," *Annu. Rev. Pharmacol. Toxicol.* 32:239–269 (1992).
CA:131:44606 abs of WO9931072 Jun. 24, 1999.*
CA:132:35516 abs of WO9964394 Dec. 16, 1999.*

* cited by examiner

*Primary Examiner*—Jean F. Vollano
(74) *Attorney, Agent, or Firm*—Michael A. Sanzo; Pillsbury Winthrop LLP

(57) ABSTRACT

Compounds of general formula I

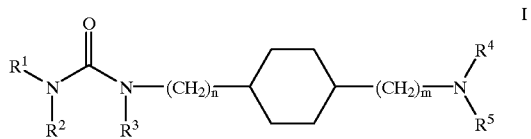

are disclosed and claimed in the present application, as well as their pharmaceutically acceptable salts, pharmaceutical compositions comprising the novel compounds and their use in therapy, in particular in the management of pain.

15 Claims, No Drawings

SUBSTITUTED UREA COMPOUNDS USEFUL IN PAIN MANAGEMENT

CROSS REFERENCE TO RELATED APPLICATIONS

The present application represents U.S. national stage of international application PCT/SE99/01077 which has an international filing date of Jun. 16, 1999 and which was published in English under Article 21(2) of the PCT on Dec. 29, 1999 as No. 9/67206. The international application claims priority to Swedish application 9802208-0, filed on Jun. 22, 1998.

FIELD OF THE INVENTION

The present invention is related to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269. for review). These compounds, e.g. naltrindole, suffer from rather poor (i.e., <10-fold) selectivity for the δ receptor vs. $\mu$ receptor binding and exhibit no analgesic activity, a fact which underscores the need for the development of highly selective non-peptidic δ ligands.

Thus, the problem underlying the present invention was to find new analgesics having improved analgesic effects, but also with an improved side-effect profile over current $\mu$ agonists and potential oral efficacy.

Analgesics that have been identified and are existing in the prior art have many disadvantages in that they suffer from poor pharmacokinetics and are not analgesic when administered by systemic routes. Also, it has been documented that preferred compounds, described within the prior art, show significant convulsive effects when administered systemically.

The problem mentioned above has now been solved by developing novel 1,4-substituted cyclohexyl compounds, as will be described below.

OUTLINE OF THE INVENTION

The novel compounds according to the present invention are defined by the general formula I

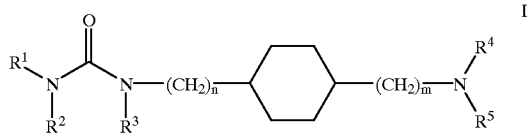

wherein
  m and n is each and independently an integer of from 0–3, and one or more of the hydrogens in such an alkylene-chain may optionally be substituted by anyone of $C_1$–$C_6$ alkyl $C_1$–$C_6$ alkoxy or hydroxy; or
  one or more of the methylene groups may optionally be substituted by a heteroatom such as O, N or S;
  $R^1$ is selected from hydrogen, a branched or straight $C_1$–$C_6$ alkyl, $C_2$–$C_6$ alkenyl, $C_3$–$C_8$ cycloalkyl, $C_4$–$C_8$ (alkyl-cycloalkyl) wherein the alkyl is $C_1$–$C_2$ alkyl and the cycloalkyl is $C_3$–$C_6$ cycloalkyl;
  $R^2$ is selected from any of
    (i) hydrogen;
    (ii) a straight or branched $C_1$–$C_6$ alkyl $C_2$–$C_6$ alkenyl or $C_2$–$C_6$ alkynyl;
    (iii) —[$(CH_2)_q$— aryl];
    (iv) —(($CH_2)_r$-heteroaryl) where the heteroaryl has from 5 to 10 atoms and the heteroatom is selected from any of S, N and O;
    and wherein the heteroaryl may optionally and independently be substituted by 1 or 2 substituents Y where each Y is as defined below; and wherein q and r is each and independently an integer of from 0 to 3;
    (v) $C_3$–$C_{10}$ cycloalkyl, optionally comprising one or more unsaturations and optionally susbtituted by one or more heteroaryl(s) where the heteroaryl has from 5 to 10 atoms and the heteroatom being selected from any of S, N and O;
    and wherein the aryl and heteroaryl may optionally and independently be substituted by 1 or 2 substituents Y where each Y is as defined below;
    (vi) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;
    (vii) heteroaryl having from 5 to 10 atoms and the heteroatom being selected from any of S, N and O; wherein the aryl and heteroaryl may optionally and independently be substituted by 1 or 2 substituents Y wherein each Y is as defined below;
    or
  $R^1$ and $R^2$ may optionally form a heterocyclic ring, which may optionally be saturated or unsaturated;
  $R^3$ is selected from anyone of
    (i) hydrogen;
    (ii) a straight or branched $C_1$–$C_6$ alkyl, $C_2$–$C_6$ alkenyl or $C_2$–$C_6$ alkynyl;
    (iii) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;
    (iv) heteroaryl-($C_5$–$C_{10}$alkyl) where the heteroaryl has from 5 to 10 atoms, the heteroatom being selected from any of S, N and O, and wherein the heteroaryl may optionally and independently be substituted by 1 or 2 substituents Y where each Y is as defined below;

(v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined below;

(vi) —[$C_3$–$C_6$ cycloalkyl-($CH_2$)$_q$] wherein q is an integer of from 1 to 3;

$R^4$ is selected from (i) hydrogen;

(ii) a straight or branched $C_1$–$C_6$ alkyl, $C_2$–$C_6$ alkenyl or $C_2$–$C_6$ alkynyl;

(iii) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;

(iv) heteroaryl-($C_5$–$C_{10}$alkyl) where the heteroaryl has from 5 to 10 atoms, the heteroatom being selected from any of S, N and O, and wherein the heteroaryl may optionally and independently be substituted by 1 or 2 substituents Y where each Y is as defined below;

(v) $C_3$–$C_{10}$ cycloalkyl, optionally comprising one or more unsaturations and optionally susbtituted by one or more heteroaryl(s) where the heteroaryl has from 5 to 10 atoms and the heteroatom being selected from any of S, N and O;

and wherein the aryl and heteroaryl may optionally and independently be substituted by 1 or 2 substituents Y where each Y is as defined below;

(vi) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;

(vii) heteroaryl having from 5 to 10 atoms, the heteroatom being selected from any of S, N and O; wherein the heteroaryl may optionally and independently be substituted by 1 or 2 substituents Y wherein each Y is as defined below;

$R^5$ is selected from anyone of (i) hydrogen;

(ii) a straight or branched $C_1$–$C_6$ alkyl, $C_2$–$C_6$ alkenyl or $C_2$–$C_6$ alkynyl;

(iii) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;

(iv) heteoaryl-($C_5$–$C_{10}$ alkyl), where the heteroaryl has from 5 to 10 atoms and the heteroatom being selected from any of S, N and O, and wherein the aryl and heteroaryl may optionally and independently be substituted by 1 or 2 substituents Y where each Y is as defined below;

(v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined below;

(vi) $C_5$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;

(vii) heteroaryl having from 5 to 10 atoms, the heteroatom being selected from any of S, N and O; wherein the heteroaryl may optionally and independently be substituted by 1 or 2 substituents Y wherein each Y is as defined below;

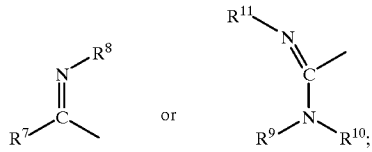

(viii)

wherein $R^7$, $R^8$, $R^9$, $R^{10}$ and $R^{11}$ is each and independently selected from (a) hydrogen;

(b) a straight or branched $C_1$–$C_6$ alkyl, $C_2$–$C_6$ alkenyl or $C_2$–$C_6$ alkynyl;

(c) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined below;

(d) heteroaryl-($C_5$–$C_{10}$alkyl), where the heteroaryl has from 5 to 10 atoms, the heteroatom being selected from any of S, N and O, and wherein the heteroaryl may optionally and independently be substituted by 1 or 2 substituents Y where each Y is as defined above;

(e) $C_3$–$C_{10}$ cycloalkyl, optionally comprising one or more unsaturations and optionally susbtituted by one or more heteroaryl(s) where the heteroaryl has from 5 to 10 atoms and the heteroatom being selected from any of S, N and O;

and wherein the aryl and heteroaryl may optionally and independently be substituted by 1 or 2 substituents Y where each Y is as defined below;

(f) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined below;

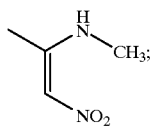

or

R⁴ and R⁵ may optionally form a heterocyclic ring, which may optionally be saturated or unsaturated;

Y is each and independently selected from any of hydrogen, $CH_3$; —$(CH_2)_{p1}CF_3$; halogen; $C_1$–$C_3$ alkoxy; hydroxy; —$NO_2$; —$OCF_3$; —$CONR^aR^b$; —$COOR^a$; —$COR^a$; —$(CH_2)_{p2}NR^aR^b$; —$(CH_2)_{p3}CH_3$, $(CH_2)_{p4}SOR^aR^b$; —$(CH_2)_{p5}SO_2R^a$; —$(CH_2)_{p6}SO_2NR^a$; $C_4$–$C_8$(alkyl-cycloalkyl) wherein alkyl is $C_1$–$C_2$ alkyl and cycloalkyl is $C_3$–$C_6$ cycloalkyl; 1 or 2 heteroaryl(s) having from 5 to 10 atoms and the heteroatom(s) being selected from any of S, N and O; and oxides such as N-oxides or sulfoxides; and wherein $R^a$ and $R^b$ is each and independently selected from hydrogen, a branched or straight $C_1$–$C_6$ alkyl, $C_1$–$C_6$ alkenyl, $C_3$–$C_8$ cycloalkyl; and wherein p1, p2, p3, p4, p5 and p6 is each and independently 0, 1 or 2.

Within the scope of the invention are also pharmaceutically acceptable salts of the compounds of the formula (I), as well as isomers, hydrates, isoforms and prodrugs thereof.

Examples of heterocyclic ring systems which ma y be formed by R² and R³ together include but are not limited to azeridine, pyrrolidine, piperidine, azepine, azocine, their hydrogenated or dehydrogenated derivatives, their amino-derivatives and other aza-heterocycle moieties and their derivatives, such as dihydroimidazoles, di-, tetra- and hexahydropyrimidines and the like.

Preferred compounds according to the invention are compounds of the formula I wherein m=n=1

$R^1$ is selected from hydrogen or $C_1$–$C_6$ alkyl;

$R^2$ is selected from
  (i) hydrogen;
  (ii) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined above;
  (iii) $C_1$–$C_6$ alkyl; or
  (iv) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined above;

$R^3$ is selected from
  (i) hydrogen;
  (ii) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
  (iii) —[$C_3$–$C_6$ cycloalkyl-$(CH_2)_q$] wherein q is an integer of from 1 to 3;

$R^4$ is hydrogen;

$R^5$ is selected from anyone of
  (i) hydrogen;
  (ii) a straight or branched $C_1$–$C_6$ alkyl, $C_2$–$C_6$ alkenyl or $C_2$–$C_6$ alkynyl;
  (iii) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
  (iv) heteroaryl-($C_5$–$C_{10}$alkyl) where the heteroaryl has from 5 to 10 atoms, the heteroatom being selected from any of S, N and O, and wherein the heteroaryl may optionally and independently be substituted by 1 or 2 substituents Y where each Y is as defined above;
  (v) $C_3$–$C_{10}$ cycloalkyl, optionally comprising one or more unsaturations and optionally substituted by one or more heteroaryl(s) having from 5 to 10 atoms and the heteroatom being selected from any of S, N and O, and wherein the aryl and heteroaryl may optionally and independently be substituted by 1 or 2 substituents Y where each Y is as defined above;
  (vi) heteroaryl having from 5 to 10 atoms, the heteroatom being selected from any of S, N, and O; wherein the heteroaryl may optionally and independently be substituted by 1 or 2 substituents Y wherein each Y is as defined above;

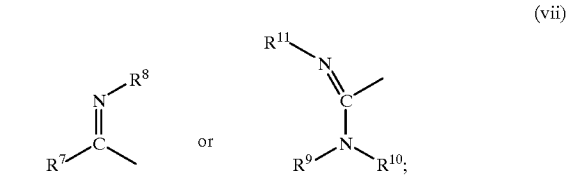

wherein $R^7$, $R^8$, $R^9$, $R^{10}$ and $R^{11}$ is each and independently selected from
  (a) hydrogen;
  (b) a straight or branched $C_1$–$C_6$ alkyl, $C_2$–$C_6$ alkenyl or $C_2$–$C_6$ alkynyl;
  (c) $C_6$–$C_{10}$ arylalkyl, wherein the aryl may optionally be substituted by one or more heteroaryl(s) having from 5 to 10 atoms and the heteroatom being selected from any of S, N and O; and wherein the aryl and heteroaryl may optionally and independently be substituted by 1 or 2 substituents Y wherein each Y is as defined above;
  (d) heteroaryl-($C_5$–$C_{10}$alkyl), where the heteroaryl has from 5 to 10 atoms, the heteroatom being selected from any of S, N and O, and wherein the heteroaryl may optionally and independently be substituted by 1 or 2 substituents Y where each Y is as defined above;
  (e) $C_3$–$C_{10}$ cycloalkyl, optionally comprising one or more unsaturations and optionally susbtituted by one or more heteroaryl(s) where the heteroaryl has from 5 to 10 atoms and the heteroatom being selected from any of S, N and O; and wherein the aryl and heteroaryl may optionally and independently be substituted by 1 or 2 substituents Y where each Y is as defined above;

(f) $C_6$–$C_{10}$ aryl, optionally and independently substituted by one or more heteroaryl(s) having from 5 to 10 atoms and the heteroatom(s) being selected from any of S, N and O and wherein the heteroaryl may optionally and independently be substituted by 1 or 2 substituents Y wherein each Y is as defined above;

(viii)

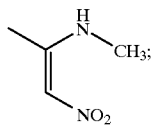

or $R^4$ and $R^5$ may optionally form a heterocyclic ring, which may optionally be saturated;

Particularly preferred compounds according to the invention are compounds of the formula I wherein m=n=1

$R^1$ is selected from
(i) hydrogen; and
(ii) methyl;

$R^2$ is selected from
(i) hydrogen;
(ii) phenyl;
(iii) $C_1$–$C_3$ alkyl;
(iv) $C_3$–$C_6$ cycloalkyl;
or $R^1$ and $R^2$ taken together may form a ring of from 4 to 6 atoms selected from C, N and O;

$R^3$ is selected from
(i) hydrogen;
(ii) —CH$_2$-cyclohexyl;
(iii) —CH$_2$-phenyl, optionally substituted by one or more halogens;
(iv) —CH$_2$-naphthyl;

$R^4$ is hydrogen;

$R^5$ is selected from
(i) hydrogen;

(ii)

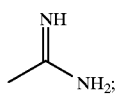

(iii)

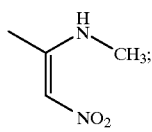

(iv) heteroaryl-($C_5$-$C_{10}$), where the heteroaryl has from 5 to 10 atoms, the heteroatom being selected from any of S, N and O, and wherein the heteroaryl may optionally and independently be substituted by 1 or 2 sustituents Y where each Y is as defined above;

By "halogen" we mean chloro, fluoro, bromo and iodo.

By "aryl" we mean an aromatic ring having 6 or 10 carbon atoms, such as phenyl and naphthyl.

By "heteroaryl" we mean an aromatic ring in which one or more of the from 5–10 atoms in the ring are elements other than carbon, such as N, S and O.

By "isomers" we mean compounds of the formula (I), which differ by the position of their functional group and/or orientation. By "orientation" we mean stereoisomers, diastereoisomers, regioisomers and enantiomers.

By "isoforms" we mean compounds of the formula I which differ in the relative physical arrangement of molecules by crystal lattice, such that isoforms refer to various crystalline compounds and amorphous compounds.

By "prodrug" we mean pharmacologically acceptable derivatives, e.g. esters and amides, such that the resulting biotransformation product of the derivative is an active form of the drug. The reference by Goodman and Gilmans, The Pharmacological basis of Therapeutics, 8th ed., McGraw-Hill, Int. Ed. 1992, "Biotransformation of Drugs, p. 13–15, describing prodrugs generally, is hereby incorporated by reference.

The novel compounds of the present invention are useful in therapy, especially for the treatment of various pain conditions such as chronic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, urinary incontinence, various mental illnesses, cough, lung oedema, various gastro-intestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. Amnesia, analgesia, muscle relaxation and sedation). Included in this combination are inhaled anaesthetics, hypnotica, anxiolytics, neuromuscular blockers and opioids.

The compounds of the present invention in isotopically labelled form are useful as a diagnostic agent.

Also within the scope of the invention is the use of any of the compounds according to the formula (I) above, for the manufacture of a medicament for the treatment of any of the conditions discussed above.

A further aspect of the invention is a method for the treatment of a subject suffering from any of the conditions discussed above, whereby an effective amount of a compound according to the formula (I) above, is administered to a patient in need of such treatment.

The best mode of performing the invention known at present, is to use the compounds according to Example 1 (compound 7); Example 2 (compound 9); Example 3 (compound 10); and Example 6 (compound 17). The numbering of the compounds is in accordance with the numbering in the Schemes presented in the following.

METHODS OF PREPARATION

The compounds of the present invention may be prepared as described in the following.

General Procedure for the Preparation of 1,4-trans-cyclohexane Derived Compounds Scheme 1

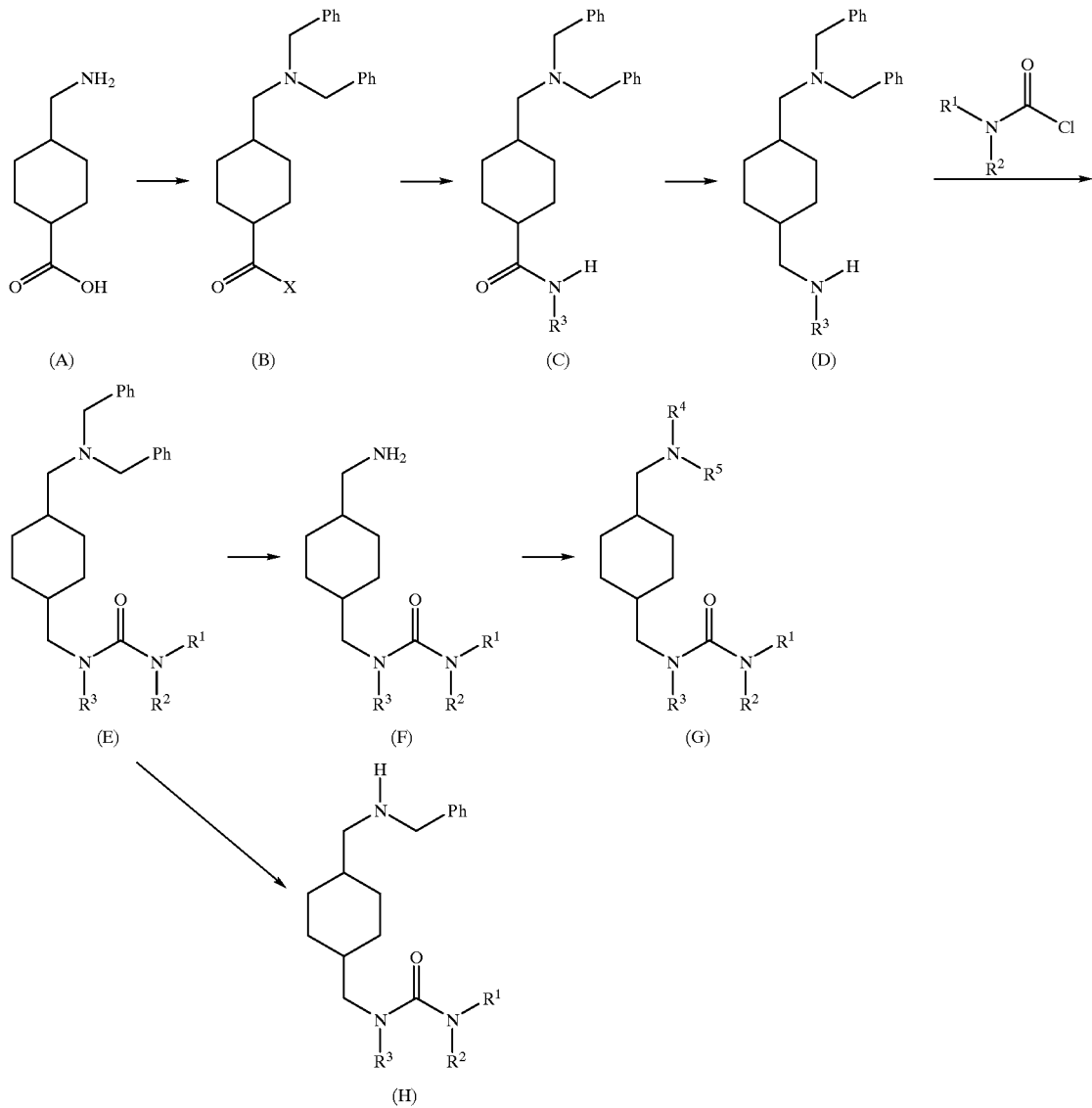

As shown in SCHEME I above, compounds of the formula (H) may be obtained from compounds of the formula (G), by deprotection by methods known in the art and exemplified in the literature, see e.g. *Protecting groups* by Green, or *Modern Synthetic Reactions* by House, which are well known to a person skilled in the art.

As shown in SCHEME I, compounds of the formula (G) may be obtained by reaction among an amine of the formula (F), and using a guanylating reagent, an amidinating reagent or an alkylating reagent. These reactions may be performed in solvents such as THF, toluene, ether, dimethylformamide, dioxane, dichloromethane or in solvents mixtures.

As shown in SCHEME I, compounds of the formula (F) and (H) may be obtained from compounds of the formula (E), by deprotection of the N,N-dibenzyl group by methods known in the art and exemplified in the literature, see, e.g.

*Protecting groups* by Green, *Modern Synthetic Reactions* by House, March, J., *Advanced Organic Chemistry* 4$^{th}$ Ed., John Wiley & Sons, 1992, which are well known to a person skilled in the art.

As shown in SCHEME I, compounds of the formula (E) may be obtained from compounds of the formula (D), and reacted with commercially available alkyl isocyanate such as phenyl isocyanate or with dialkylcarbamoyl chloride, prepared by methods known in the art literature (March, J., *Advanced Organic Chemistry* 4$^{th}$ Ed., John Wiley & Sons, 1992) or the like in presence of a base such as triethylamine, $Na_2CO_3$, $K_2CO_3$, $K_3PO_4$, CsF, NaOH, DIPEA or the like. The reaction may be carried out in solvents such as THF, dichloromethane, toluene, ether, dimethylformamide, dioxane, or in solvents mixtures.

As shown in SCHEME I, compounds of the formula (D) may be obtained from a reduction of an amide of the formula (C). The reduction step may be performed with a reducing agent commercially available such $LiAlH_4$, $BH_3$, NaBH₃CN or the like in the presence of solvent such as THF, dioxane, ether, dichloromethane toluene or in a solvents mixtures.

As shown in the SCHEME I, compounds of the formula (C) may be obtained by reactions among a carbonyl compound of the formula (B) wherein X is a suitable leaving group such as chloro, bromo, hydroxy or the like, and with an alkyl amine such as 2,2-diphenylethylamine and cyclohexanemethylamine or the like. The reaction may be performed in solvents such as THF, toluene, ether, dimethylformamide, dioxane, dichloromethane or solvents mixtures.

As shown in SCHEME I, compounds of the formula (B) may be obtained by protecting a commercially available amine compound of the formula (A), by methods known in the art and exemplified in the literature, see e.g. *Protecting groups* by Green, or *Modern Synthetic Reactions* by House, followed by acid activation using a chloroformate such as isobutylchloroformate in a solvent such as THF.

In Scheme I above R¹, R², R³, R⁴, R⁵ and R⁵ are as defined in formula I above.

General Procedure for the Preparation of 1,4-cis, trans-cyclohexane Derived Compounds Scheme 2

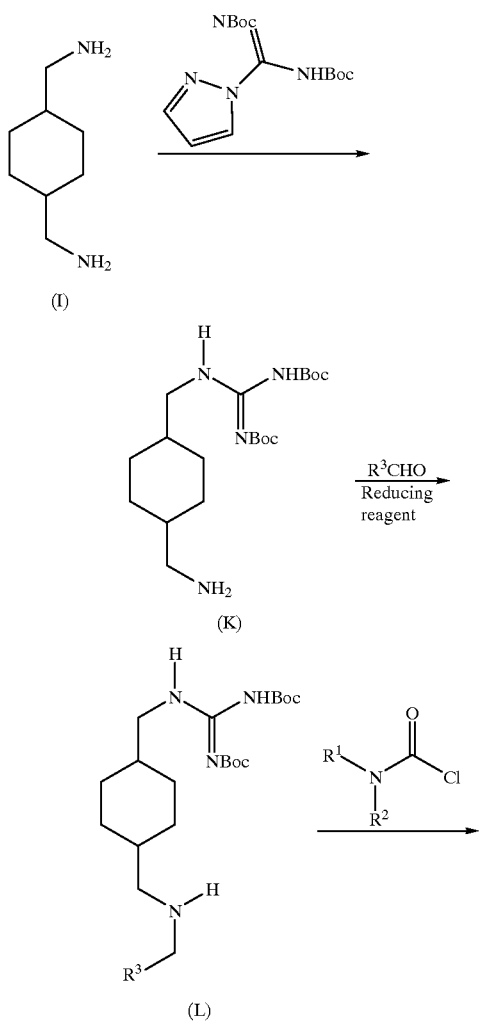

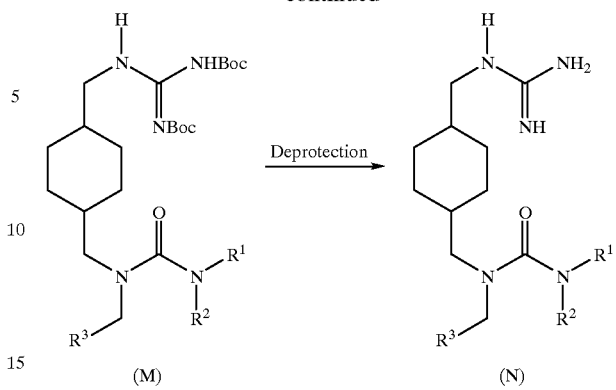

Compounds of the general formula N may be prepared by following the procedure described in Scheme 2 below.

A commercially available cis/trans mixture of 1,4-bis-aminomethyl cyclohexane (compound I) is converted into mono-(diBoc)-guanidinomethyl derivative K using a protected guanylating reagent such as 1-H-pyrazole-1-(N,N-bis(tert-butoxycarbonyl)carboxamidine in an organic solvent such a THF.

The secondary amine (compound L) may be generated using a reductive amination step, where compound K is treated with an aldehyde in the presence of an acid such as acetic acid or ZnCl₂ in a protic solvent such as methanol or ethanol in the presence of a reducing agent such as sodium cyanoborohydride.

Compounds of the general formula M may be obtained by performing an urea reaction where compound L is reacted with a dialkylcarbamoyl chloride such as N-methyl-N-phenyl-carbamoylchloride in a solvent such as methylene chloride and in the presence of a tertiary amine such as triethylamine or the like.

Finally, compound of the general formula N may be obtained by cleavage of the Boc protecting groups, using an acid such as trifluoroacetic acid or aqueous hydrochloric acid.

In Scheme I above R¹, R², and R³ are as defined in formula I above.

EXAMPLES

The invention will now be described in more detail by way of the following Examples, which are not to be construed as limiting the invention in any way.

Scheme 3

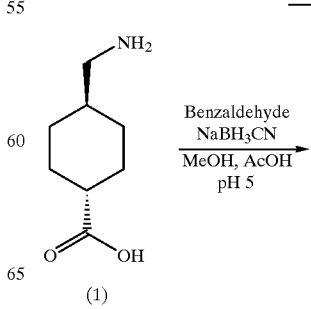

-continued
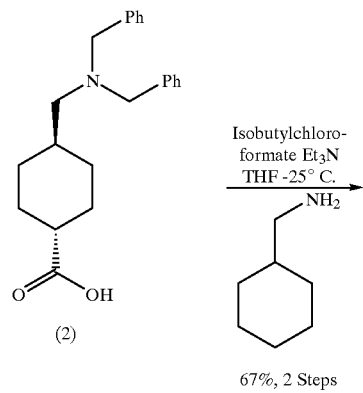
(2)
Isobutylchloro-
formate Et₃N
THF -25° C.
→
NH₂–CH₂–cyclohexyl
67%, 2 Steps
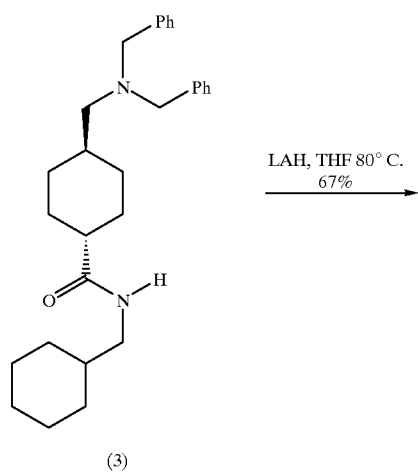
(3)
LAH, THF 80° C.
67%
→
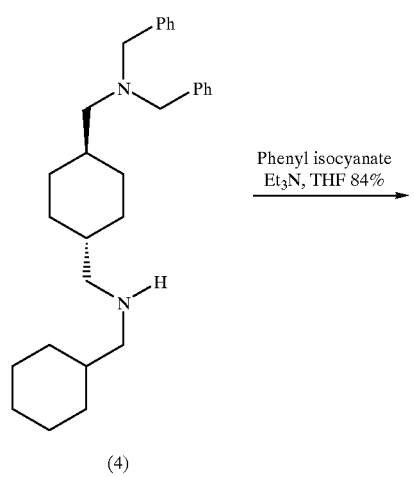
(4)
Phenyl isocyanate
Et₃N, THF 84%
→
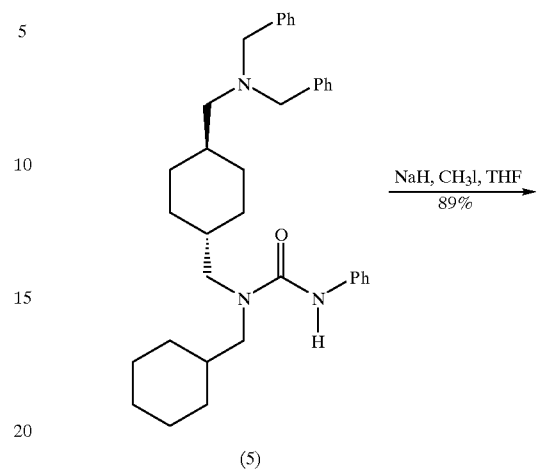
(5)
NaH, CH₃I, THF
89%
→
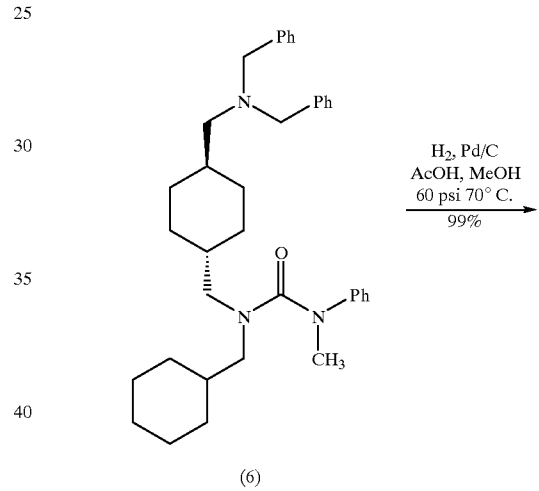
(6)
H₂, Pd/C
AcOH, MeOH
60 psi 70° C.
99%
→
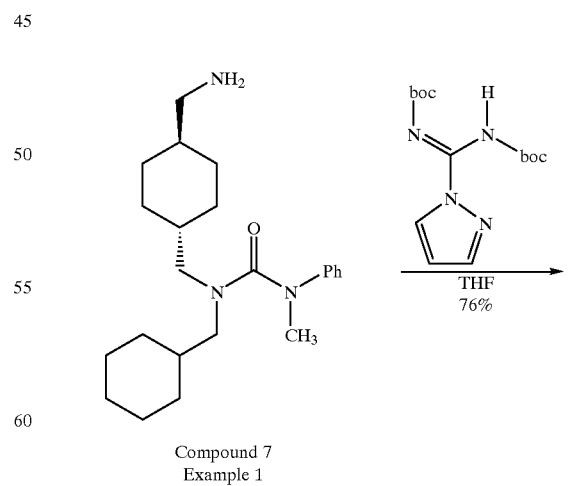
Compound 7
Example 1
THF
76%
→

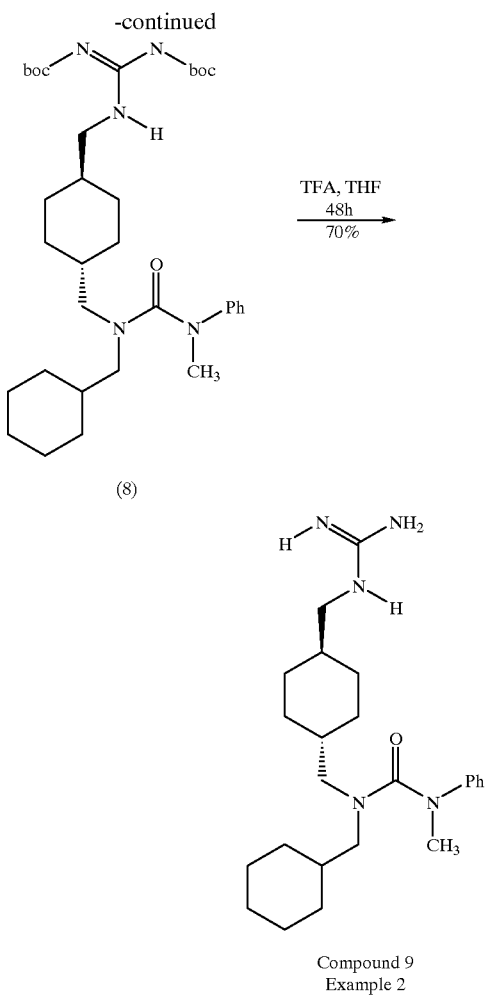

Compound 9
Example 2

Example 1

Preparation of trans-1-N-(Cyclohexlmethyl)-N-(N-methyl-N-phenyl carbamoyl)-aminomethyl-4-aminomethyl Cyclohexane (Compound 7)

Compound 7 of Example 1 was prepared as follows.
Step 1
Preparation of trans-4,N,N-(Dibenzyl)-aminomethyl Cyclohexane Carboxylic Acid (Compound 2)

To a suspension of (40.0 g, 254 mmol) of trans-4-(Aminomethyl)cyclohexanecarboxylic (compound 1) acid, in 1.5 L of methanol was added benzaldehyde (60 ml, 590 mmol) followed by sodium cyanoborohydride (16 g, 254 mmol). The pH was then adjusted to approx. 5 with glacial acetic acid. The reaction was allowed to stir for 48 hrs, during which the pH is monitored and adjusted to 5 as needed, after which the reaction volume was then decreased and the pH adjusted to 9 with 1 N NaOH. The reaction was then extracted repeatedly with diethyl ether. The organic layers were combined, washed with brine, dried over $Na_2SO_4$, filtered and concentrated. The resulting product solidifies on standing and was recrystallized from methanol giving 32 g of impur product which was used without further purification in the next step.

The monobenzyl was isolated as a white solid which formed during the extraction and was collected by filtration. (8.2 g)

Monobenzyl $^1$H NMR: ($D_2O$) δ (ppm): 7.40–7.20 (5H, m, Ar), 4.06 (C$\underline{H}_2$Ar, 5H, s), 2.75 (2H, d, J=7.2, NC$\underline{H}_2$), 1.95–1.85 (1H, m), 1.75–1.72 (2H, m), 1.64–1.62 (2H, m), 1.56–1.51 (1H, m), 1.22–1.11 (2H, m), 0.91–0.81 (2H, m).
$^{13}$C NMR: ($D_2O$, DSS) δ (ppm): 31.43 ($CH_2$), 31.88 ($CH_2$), 36.81 (CH), 48.95 (CH), 54.01 ($NCH_2$), 55.35 ($NCH_2$), 131.94 (CH), 132.37 (CH), 132.60 (CH), 133.30 (C), 188.43 (C=O).

Step 2
Preparation of trans-1-N-(Cyclohexlmethyl)-4-N,N-(dibenzyl)-aminomethyl Cyclohexane Carboxamide (Compound 3)

To a solution of compound 2 prepared in the previous step 1 (2.18 g, 647 mmol), in dry THF (10 ml) at −25° C., was added triethylamine (1.08 ml, 7.76 mmol) followed by isobutylchloroformate (1.0 ml, 7.76 mmol). The reaction mixture was stirred at −25° C. for 30 min. A white precipitate was formed during the reaction.

The cyclohexanemethylamine (1.26 ml, 9.71 mmol) was added dropwise via syringe. The reaction mixture was warmed up to r.t., stirred for 1 h, and then quenched with saturated aqueous $NH_4Cl$ solution, and extracted with $CH_2Cl_2$. The organic layer was dried over anhydrous $MgSO_4$ and concentrated to give a crude product, which was further purified by silica gel column chromatography using hexane-AcOEt (4:1"1:1) to provide the title product (compound 3), (1.86 g, 67%).

$^1$H NMR: ($CDCl_3$, TMS) δ (ppm): 7.36–7.20 (10H, m, Ar), 5.40 (1H, s, br, N$\underline{H}$), 3.51 (4H, s, C$\underline{H}_2$Ph), 3.07 (2H, t, C$\underline{H}_2$N), 2.19 (2H, d, C$\underline{H}_2$N), 2.20–1.87 (5H, m), 1.73–1.58 (8H, m), 1.44–1.41 (2H, m), 1.23–1.15 (2H, m), 0.92–0,90 (2H, m), 0.76–0,72 (2H, m)

Step 3
Preparation of trans-1-N-(Cyclohexylmethyl)-aminomethyl-4-N,N-(dibenzyl)aminomethyl Cyclohexane (Compound 4)

To a solution of compound 3 (1.85 g, 4.28 mmol) prepared in the previous step 2, in dry THF (20 ml) at r.t., was added slowly LAH (490 mg, 12.84 mmol). The reaction mixture was heated at reflux 80° C. overnight. The mixture was then cooled down at r.t., quenched with MeOH until no hydrogen formation evolved and then 1 N HCl was added to dissolve the precipitate. The gray mixture was extracted with $CH_2Cl_2$ and AcOEt. The organic layer was dried over anhydrous $MgSO_4$ and concentrated to give (1.2 g, 67% ) of white solid (compound 4).

$^1$H NMR: ($CDCl_3$, TMS) δ (ppm): 9.2 (1H, s, br, N$\underline{H}$), 7.66 (4H, s, Ar), 7.44 (6H, s, Ar), 4.54 (2H, s, br, C$\underline{H}_2$N), 4.14 (2H, s, br, C$\underline{H}_2$N), 2.75 (6H, s, br, C$\underline{H}_2$Ph, C$\underline{H}_2$N), 1.99–1.90 (9H, m), 1.80–1.60 (4H, m), 1.27–1.02 (6H, m), 0.83–0.80 (2H, m).

Step 4
Preparation of trans-1-N-(Cyclohexylmethyl)-N-(N-phenylcarbamoyl)-aminomethyl-4-N,N-(dibenzyl)aminomethylcyclohexane (compound 5)

To a solution of (compound 4) (500 mg, 1.2 mmol) in dry THF (12 ml) and $CH_2Cl_2$ (3 ml) at r.t. was added triethylamine (167 μl, 1.2 mmol) followed by phenylisocyanate (195 μl, 1.79 mmol).

The reaction mixture was stirred 2 h at r.t., quenched with aqueous $NH_4Cl$ solution then extracted with AcOEt. The organic layer was dried over anhydrous $MgSO_4$ and concentrated to give the crude product which was further purified by silica gel column chromatography using hexane-AcOEt (9:1) to provide the title product (compound 5) (545 mg, 84%).

$^1$H NMR: ($CDCl_3$, TMS) δ (ppm): 7.38–7.19 (15 H, m, Ar) 3.50 (4H, s, C$\underline{H}_2$Ph), 3.15–3.11 (4H, m, C$\underline{H}_2$N), 2.19

(2H, d, CH₂N), 1.93–1.90 (2H, m), 1.78–1.55 (9H, m), 1.28–1.18 (4H, m), 0.95–0.90 (4H, m), 0.76–0.70 (2H, m).

Step 5

Preparation of trans-1-N-(Cyclohexylmethyl)-N-(N-methyl-N-phenyl carbamoyl)-aminomethyl 4-N,N-(dibenzyl) aminomethyl Cyclohexane (Compound 6)

To a solution of (compound 5) (702 mg, 1.31 mmol) prepared in the previous step 4, in dry THF (25 ml) at r.t., was added NaH 60% in mineral oil (1.56 mg, 3.92 mmol). The reaction mixture was stirred 30 min then methyl iodide (243 μl, 3.92 mmol) was added dropwise via syringe. The reaction mixture was stirred 1 h at r.t., quenched with aqueous NH₄Cl solution, and extracted with AcOEt. The organic layer was dried over anhydrous MgSO₄ and concentrated to give the crude product, which was further purified by silica gel column chromatography using hexane-AcOEt (85:15) to provide the title product (compound 6) as a colorless viscous oil (645 mg, 89%).

¹H NMR: (CDCl₃, TMS) δ (ppm): 7.37–7.04 (15H, m, Ar), 3.50 (4H, s, CH₂Ph), 3.15 (3H, s, CH₃), 2.86–2.81 (4H, m, CH₂N), 2.18 (2H, m, CH₂N), 1.90–1.86 (2H, m), 1.68–1.46 (9H, m), 1.26–1.13 (4H, m), 0.83–0.68 (6H, m).

Step 6

Preparation of trans-1-N-(Cyclohexylmethyl)-N-(N-methyl-N-phenyl carbamoyl)-aminomethyl-4-aminomethyl Cyclohexane (Compound 7)

The product (compound 6) (1.19 g, 2.16 mmol) prepared in the previous step 5, was dissolved in AcOH (20 ml) and palladium on activated carbon 10% (240 mg) was added to the solution. The mixture was stirred overnight with 60 psi of hydrogen, 4 h at 50° C. and 4 h at 70° C. The mixture was then cooled down and filtered over celite pad and the solvent removed under reduced pressure. The crude product was dissolved in CH₂Cl₂ and the organic phase washed with saturated aqueous NaHCO₃ solution. The organic layer was dried over anhydrous MgSO₄ and concentrated to give the pure desired product (compound 7) (795 mg, 99%) as a yellow viscous oil.

¹H NMR: (CDCl₃, TMS) δ (ppm): 7.35–7.23 (2H, m, Ar), 7.12–7.03 (3H, m, Ar), 3.16 (3H, s, CH₃), 2.90–2.82 (4H, m, CH₂N), 2.57–2.52 (2H, m, CH₂N), 1.90–150 (11H, m), 1.28–1.05 (6H, m), 0.93–0.79 (6H, m).

Example 2

Preparation of trans-1-N-(cyclohexylmethyl)-N-(N-methyl-N-phenylcarbamoyl)-aminomethyl-4-guanidinomethyl Cyclohexane (Compound 9)

Compound 9 of Example 2 was prepared as follows.

Step 1

Preparation of trans-1-N4cyclohexylmethyl)-N-(N-methyl-N-phenylcarbamoyl)-aminomethyl-4-(di-t-butyl carbonyloxy)-guanidinomethyl Cyclohexane (Compound 8)

To a solution of (compound 7) (459 mg, 1.24 mmol) prepared in Example 1, in dry THF (15 ml) at r.t., was added 1-H-pyrazole-1-(N,N-bis(tert-butoxycarbonyl) carboxamidine) (413 mg, 1.48 mmol). The mixture was stirred overnight and concentrated under reduced pressure. The crude product was purified by silica gel column chromatography using hexane-AcOEt (9:1) to provide the desired product (compound 8) (548 mg, 76%) as a white foam.

¹H NMR: (CDCl₃, TMS) δ (ppm): 8.38 (1H, s, br, NH), 7.34–7.26 (2H, m, Ar), 7.13–7.05 (3H, m, Ar), 3.29–3.25 (2H, m, CH₂N), 3.16 (3H, s, CH₃), 2.89–2.83 (4H, m, CH₂N), 1.81–1.78 (2H, m), 1.69–1.46 (27H, m, C(CH₃)₃), 1.26–1.13 (4H, m), 0.99–078 (6H, m).

Step 2

Preparation of trans-1-N-(cyclohexylmethyl)-N-(N-methyl-N-phenylcarbamoyl)-aminomethyl-4-guanidinomethyl Cyclohexane (Compound 9)

To a solution of (compound 8) (548 mg, 0.89 mmol) prepared in the previous step 1, in dry CH₂Cl₂ (5 ml), was added TFA (15 ml) at r.t. The reaction mixture was stirred 2 days and concentrated under reduced pressure. The resulting mixture was dissolved in CH₂Cl₂ and washed with saturated aqueous NaHCO₃ solution. The organic layer was dried over anhydrous MgSO₄ concentrated and the resulting mixture was purified by silica gel column chromatography using MeOH-CH₂Cl₂ (9:1) to provide the desired product (compound 9) (280 mg, 70%) as a light yellow oil.

¹H NMR: (CDCl₃, TMS) δ (ppm): 7.64 (1H, s, br, NH), 7.34–7.27 (2H, m, Ar), 7.14–7.03 (6H, m, Ar, NH), 3.13 (3H, s, CH₃), 3.00 (2H, s, br, CH₂N), 2.87–2.80 (4H, m, C HN), 1.79–1.50 (12H, m), 1.21–0.78 (9H, m).

Example 3

Preparation of trans-1-N-(4-chlorobenzyl)-N-(N-methyl-N-phenylcarbamoyl)-aminomethyl-4-guanidinomethyl cyclohexane (compound 10)

(10)

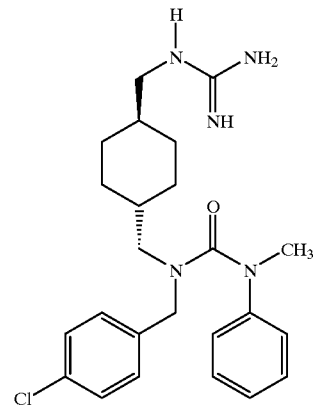

By following the same procedure as described in Example 1, step 2 but substituting cyclohexanemethylamine for 4-chlorobenzoylamino followed by step 3–6, and step 1–2 from Example 2, the compound (10) was also prepared.

¹H NMR (MeOD-d₄) δ 7.35 (m, 4H), 7.17 (m, 3H), 7.0 (t, 2H), 4.25 (s, 2H), 3.15 (d, 3H), 3.0 (t, 3H), 2.85 (d, 2H), 1.85 (d, 2 H), 1.75 (d, 3H), 1.6 (broad, 2H), 0.9 (m, 6H). MS: 442.24 (M+H).

Example 4

Preparation of trans-1-[N-(2,2-diphenylethyl)-N-morpholine-carbamoyl]-aminomethyl-4-guanidinomethyl Cyclohexane Hydrochloride (Compound 11)

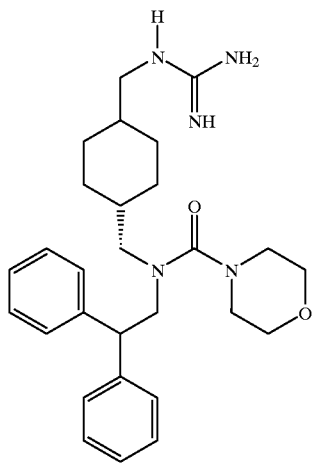

(11)

Compound 11 was obtained by following the procedure described for Example 1, step 4, but substituting phenylisocyanate for morpholine carbamoyl chloride, and substituting compound 4 for trans4-N-(diBoc)guanidinomethyl-1-N-(2,2-diphenylethyl)aminomethyl cyclohexane, followed by cleavage of Boc-groups using the procedure described in Example 2, step 2.

$^1$H NMR (CDCl$_3$) δ 8.4 (t, 1H) 7.15–7.35 (m, 10H), 4.35 (t, 1H), 3.85 (d, 2H), 3.52 (t, 4H), 3.27 (t, 2H), 2.95 (d, 6H), 1.8 (m, 6H), 1.5 (d, 18H), 0.85 (m, 4H). MS (APCI): 687.5 (M+H).

MS (APCI): 478.5.

Example 5

Preparation of 1-N-(4-chlorobenzyl)-N-(N-methyl-N-phenylcarbamoyl)-aminomethyl-4-guanidinomethyl Cyclohexane (Compound 16)

Compound 16 of this Example was prepared by following the synthetic route described in Scheme 4 below.

Scheme 4

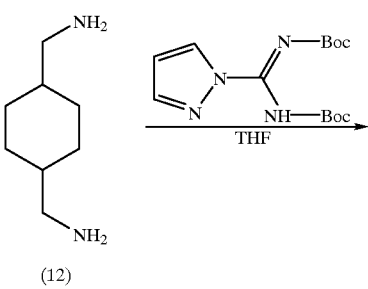

(12)

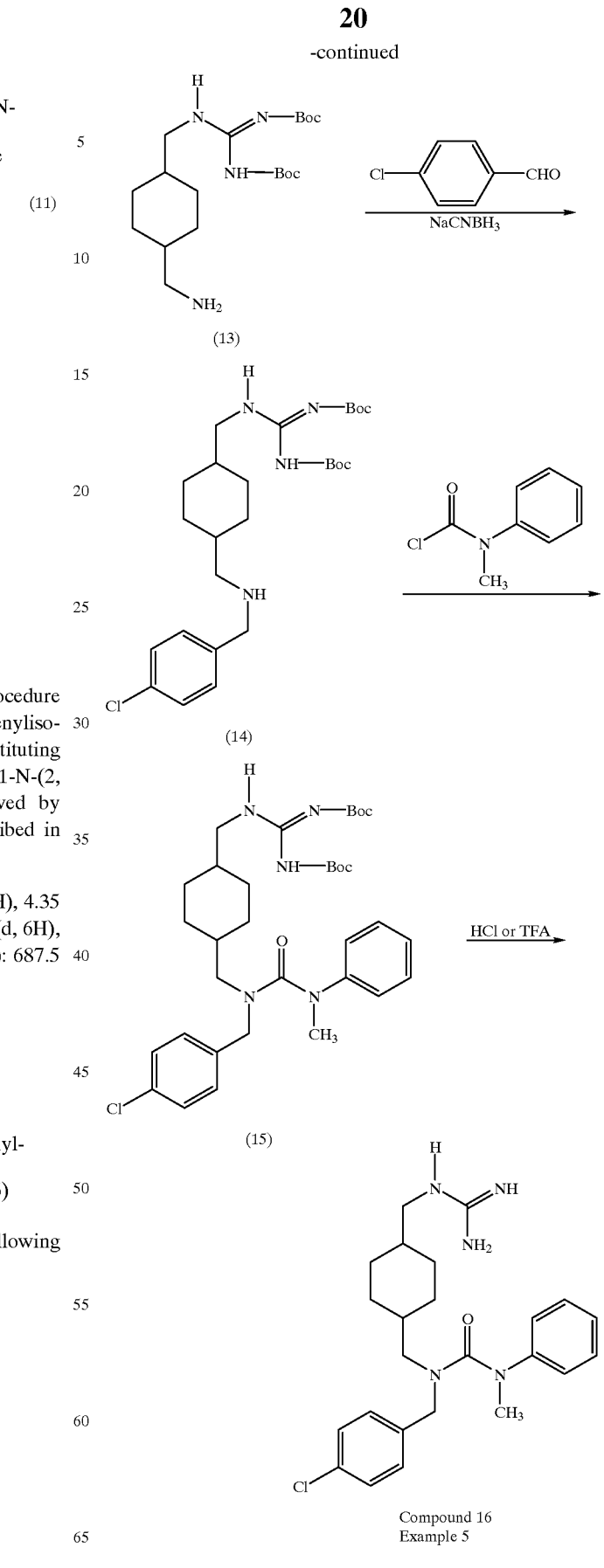

Compound 16
Example 5

Step 1
Preparation of 4-aminomethyl-1-(diBoc)-guanidinomethyl Cyclohexane (Compound 13)

Part A

1-H-pyrazole-1-carboxamidine was prepared according to Bernatowicz et. al., J. Org. Chem. 1992, 57, pp.2497–2502, and protected with di-tert-butyl dicarbonate to give 1-H-pyrazole-1-(N,N-bis(tert-butoxycarbonyl)carboxamidine according to Drake et. al, Synth. 1994. pp.579–582.

Part B

Step 1

To a solution of 1,4-bis-aminomethyl-cyclohexane (compound 12) (20 g, 0.14 mol) in THF (200 mL) was added a solution of 1-H-Pyrazole-1-(N,N-bis(tert-butoxycarbonyl)carboxamidine (22.0 g, 0.07 mol) in THF (100 mL). The solution was stirred at room temperature for 3 hrs. The solvent was removed under reduced pressure to give a syrupy residue which was taken up in ethyl acetate and washed with water until neutral pH. The organic layer was washed with brine, dried over MgSO$_4$ and concentrated. The product (compound 13) was purified by column chromatography on silica gel using a mixture of methylene chloride:methanol as the eluent to afford 11.6 g (43% yield) of 1-(diBoc)-guanidinomethyl-4-aminomethyl cyclohexane.

$^1$H NMR (CDCl$_3$) δ 3.26 (d of t, 2H), 2.52 (d of d, 2H), 1.82–0.97 (m, 28H, with singlet at 1.5).

Step 2
Preparation of (1-N-4-chlorobenzyl)-aminomethyl-4-N-(diBoc)-guanidinomethyl Cyclohexane (Compound 14)

To a solution of 1-(diBoc)-guanidinomethyl-4-aminomethyl cyclohexane (compound 13) (1 eq) in methanol containing 1% (v/v) of glacial acetic acid (alternatively, ZnCl$_2$ can be used) was added 4-chlorobenzaldehyde (1 eq), followed by NaBH$_3$CN (3–4 eq). The reaction mixture was stirred at room temperature overnight. The reaction was quenched with water, basified with aqueous NaHCO$_3$ solution and extracted with methylene chloride. The organic layer was washed with brine, dried over MgSO$_4$ and concentrated. The product (compound 14) was chromatographed on silica gel using a mixture of hexane:ethyl acetate as the eluent.

Step 3
Preparation of 1-N-(4-chlorobenzyl)-N-(N-methyl-N-phenylcarbamoyl)-aminomethyl-4-N-(diBoc)-guanidinomethyl Cyclohexane (Compound 15)

To a solution of secondary amine (compound 14 Scheme 4) (1 eq) in dioxane or methylene chloride was added triethylamine (1.5–2.0 eq), followed by the N-methyl-N-phenyl carbamoylchloride (1 eq). The reaction mixture was stirred at room temperature for 3 h overnight, then basified with 1N K$_2$CO$_3$ solution and extracted with ethyl acetate. The organic layer was washed with brine, dried over MgSO$_4$, concentrated and chromatographed on silica gel or purified by preparative TLC using a mixture of hexane-ethyl acetate as the eluent.

Step 4
Preparation of 1-N-(4-chlorobenzyl)-N-(N-methyl-N-phenylcarbamoyl)-aminomethyl-4-guanidinomethyl Cyclohexane (Compound 16)

The diBoc-guanidino compound (compound 15 Scheme 4) was dissolved in 4N HCl in dioxane or 50% trifluoroacetic acid in methylene chloride and stirred at room temperature for 2 h—overnight. The solvent was removed under reduced pressure. The residue was dissolved in water and lyophylized. The product (compound 16 in Scheme 4) may also (when appropriate) be purified by reversed-phase HPLC using acetonitrile-water as the eluent.

$^1$H NMR (pyridine) δ 7.0–7.45 ( m, 9H), 4.35 (d, 2H), 3.35 (t, 2H), 3.15 (s, 3H), 3.05 (d, 1H), 2.85 (d, 1H), 0.8–2.0 (m, 10H).

MS: 442.06 (M+H).

Example 6

Preparation of 1-N-[(N-Methyl-N-Phenylcarbamoyl)-(1-naphthylmethyl)]aminomethyl-4-guanidinomethyl Cyclohexane (Compound 17)

(17)

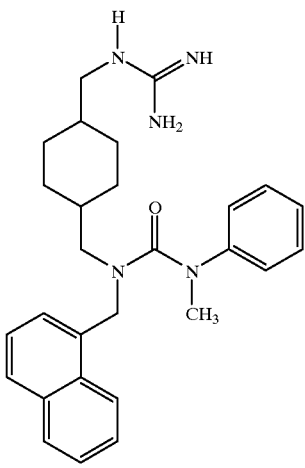

Following the procedure described for the preparation of compound 16 of Example 5, but using 1-naphtaldehyde in step 2 followed by step 3–4, the title compound 17 was obtained.

MS(APCI): 458.2 (M+H).

Example 7

Preparation of 1-N-[(N-methyl-N-phenylcarbamoyl)-(2-naphthylmethyl]aminomethyl-4-guanidinomethyl Cyclohexane (Compound 18)

(18)

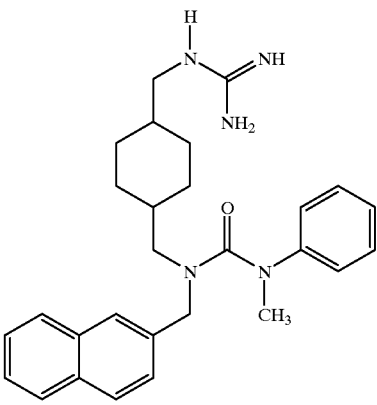

Following the procedure described for the preparation of compound 16 in Example 5, but using 2-naphtaldehyde in step 2 followed by step 3–4, the title compound 18 was obtained.

$^1$H NMR (pyridine) δ 7.95 (d, 2H), 7.0–7.7 (m, 10H), 4.55 (s, 2H), 3.25 (s, 3H), 3.10 (m, 2H), 2.95 (d, 2H), 0.8–2.0 (m, 10H). MS(APCI): 442.01 (M +H)

Scheme 5
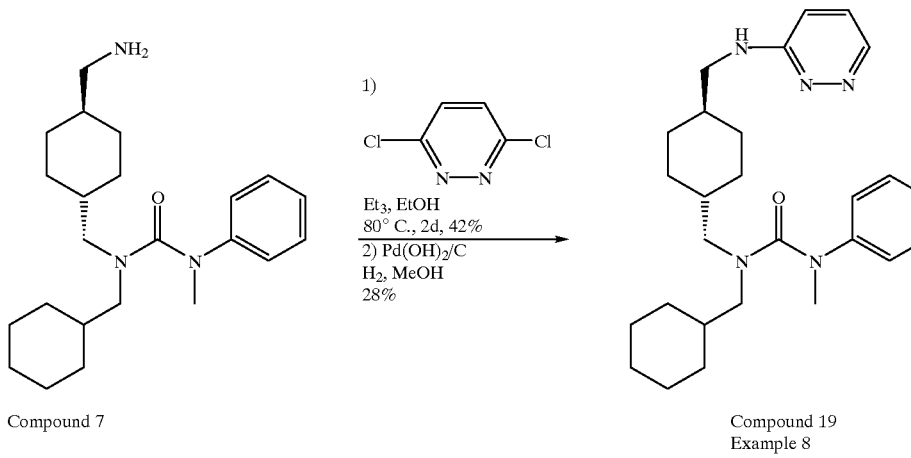
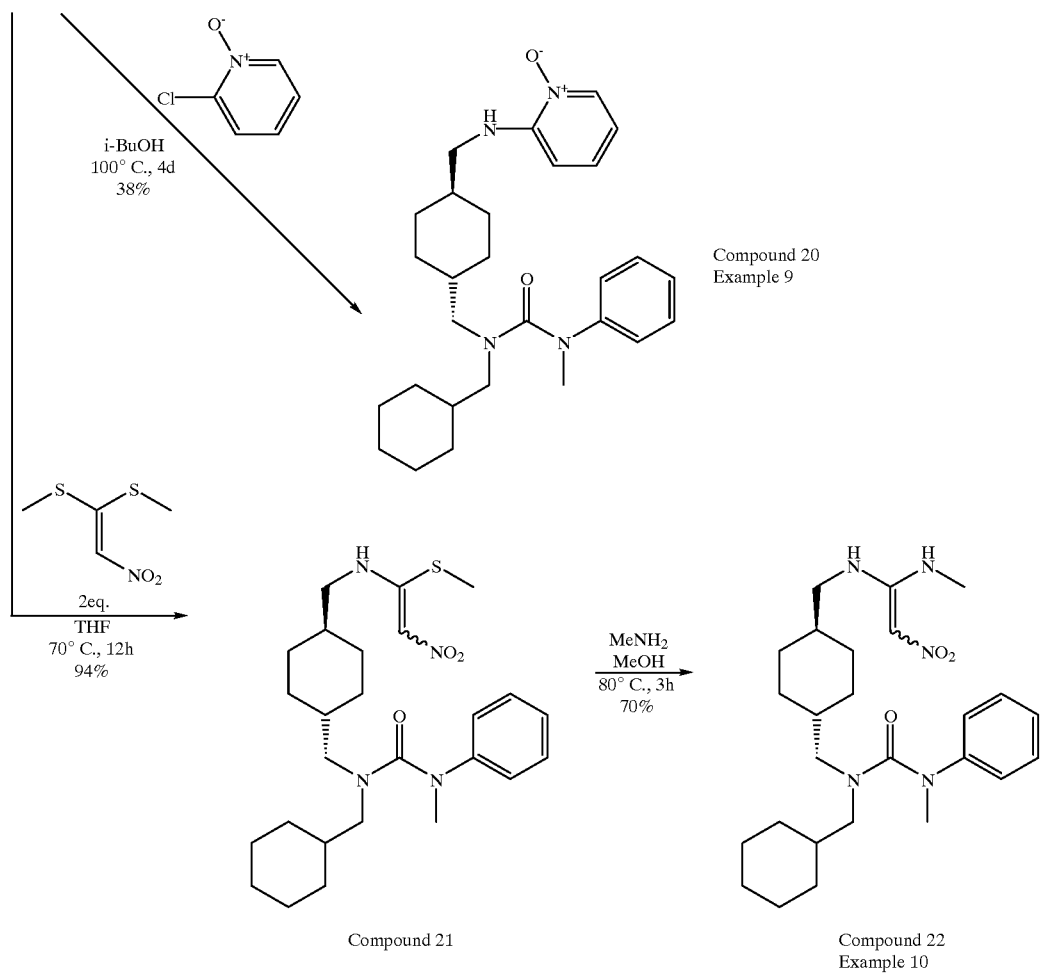

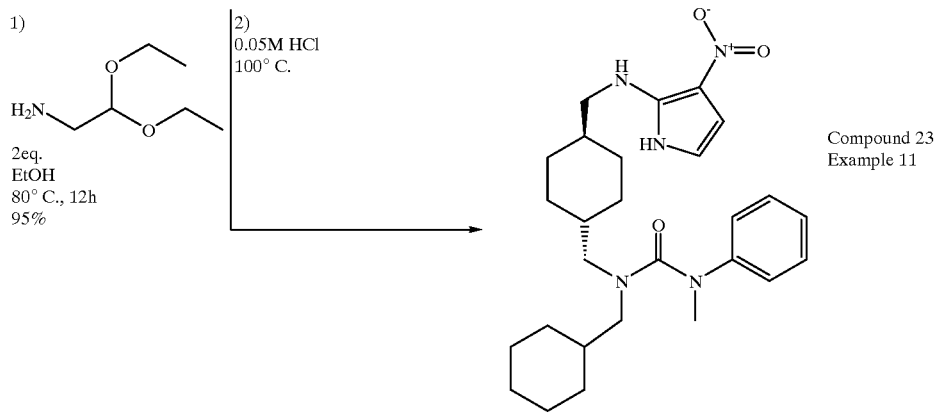

Compound 23
Example 11

Example 8

Preparation of N-(Cyclohexylmethyl)-N'-methyl-N'-phenyl-N-({4-[(3-pyridazinylamino)methyl]-cyclohexyl}methyl)urea (Compound 19)

Compound 7 (0.23 g, 0.62 mmol) was mixed with 3,6-dichloropyridazine and Et$_3$N (0.17 mL, 1.2 mmol) and heated in EtOH (2 mL) at 80° C. for 2 days. The solvent was evaporated and the residue purified by chromatography on silica (0 to 100% EtOAc in heptane) to give 0.13 g solid. 0.11 g of this solid was used for hydrogenolysis (H$_2$, 30 psi) with 20% palladium hydroxide on carbon (Pearlmans catalyst) (100 mg) in methanol (10 mL) for 4 h at 25 ° C., filtration and evaporation of solvent was followed by chromatography on silica (0 to 5% MeOH in CH$_2$Cl$_2$) to give compound 19 (32 mg, 12%).

$^1$H NMR (CDCl$_3$) δ 0.7–1.8 (m, 21H), 2.80 (m, 4H), 3.10 (s, 3H), 3.19 (m, 2H), 4.83 (m, 1H), 6.56 (m, 1H), 7.00–7.30 (m, 6H), 8.47 (m, 1H). MS 450.52 (M+H).

Example 9

Preparation of 2-({[4-({(Cyclohexylmethyl)[(methylanilino)carbonyl]amino}methyl)cyclohexyl]-methyl}amino)-1-pyridiniumolate (Compound 20)

Compound 7 (0.23 g, 0.62 mmol) was mixed with 2-chloropyridine-N-oxide hydrochloride (0.21 g, 1.2 mmol) and Et$_3$N (0.17 mL, 1.2 mmol) and heated in i-buOH (2 mL) at 100 ° C. for 2 days. Another portion of 2-chloropyridine-N-oxide hydrochloride and Et$_3$N was added and heating continued 2 days. The solvent was evaporated and the residue purified by chromatography on silica (0 to 10% MeOH in CH$_2$Cl$_2$) to give compound 20 (0.11 g, 38%).

$^1$H NMR (CDCl$_3$) δ 0.7–1.9 (m, 21H), 2.85 (m, 4H), 3.10 (m, 2H), 3.18 (s, 3H), 6.56 (m, 2H), 6.90 (m, 1H), 7.04–7.36 (m, 6H), 8.10 (m, 1H). MS 465.50 (M+H).

Preparation of N-(Cyclohexylmethyl)-N'-methyl-N-{[4-({[1-(methylsulfanyl)-2-nitroethenyl]-amino}methyl)cyclohexyl]methyl}-N'-phenylurea (Compound 21)

Compound 7 (0.48 g, 1.3 mmol) was mixed with 1,1-bis(methylsulfanyl)-2-nitroethylene (0.24 g, 1.4 mmol) and heated in THF (10 mL) at 70 ° C. After 4 h, another portion of 1,1-bis(methylsulfanyl)-2-nitroethylene was added and heating continued 12 h. The solvent was evaporated and the residue purified by chromatography on silica (0 to 10% MeOH in CH$_2$Cl$_2$) to give compound 21 (0.60 g, 94%).

$^1$H NMR (CDCl$_3$) δ 0.7–1.8 (m, 21H), 2.38 (s, 3H), 2.81 (m, 4H), 3.11 (s, 3H), 3.22 (m, 2H), 6.52 (s, 1H), 6.98–7.30 (m, 5H), 10.60 (s, 1H). MS 489.50 (M+H).

Example 10

Preparation of N-(Cyclohexylmethyl)-N'-methyl-N-{[4-({[1-(methylamino)-2-nitroethenyl]-amino}methyl)cyclohexyl]methyl}-N'-phenylurea (Compound 22)

Compound 21 (0.23 g, 0.47 mmol) was dissolved in a 2M solution of MeNH$_2$ in MeOH (5 mL) and heated in a sealed tube at 80 ° C. for 3 h. The solvent was evaporated and the residue purified by chromatography on silica (0 to 10% MeOH in CH$_2$Cl$_2$) to give compound 22 (0.15 g, 70%).

$^1$H NMR (CDCl$_3$) δ 0.7–1.9 (m, 21H), 2.85 (m, 4H), 3.11 (m, 2H), 3.16 (s, 3H), 6.61 (s, 1H), 6.71, 6.85 (2m, 1H), 7.02–7.36 (m, 5H), 10.20 (s, 1H). MS 472.49 (M+H).

Example 11

Preparation of N-(Cyclohexylmethyl)-N'-methyl-N-[(4-{[(3-nitro-1H-pyrrol-2-yl)amino]methyl}-cyclohexyl)methyl]-N'-phenylurea (Compound 23)

Compound 21 (0.60 g, 1.2 mmol) and 2,2-diethoxy-1-ethanamine (0.35 mL, 2.4 mmol) was dissolved in EtOH (10 mL) and heated in a sealed tube at 80 ° C. for 12 h. The solvent was evaporated and the residue purified by chromatography on silica (0 to 10% MeOH in CH$_2$Cl$_2$) to give 0.67 g. 0.34 g of this solid was refluxed in 0.05 N HCl for 2 h. Neutralisation and extraction with EtOAc gave a crude product wich was purified on silica (0 to 100% EtOAc in heptane to give compound 23 (35 mg, 12%)

$^1$H NMR (CDCl$_3$) δ 0.7–1.9 (m, 21H), 2.85 (m, 4H), 3.16 (s, 3H), 3.25 (m, 2H), 6.16 (d, 1H), 6.42 (d, 1H), 7.02–7.36 (m, 5H), 7.69 (m, 1H), 9.60 (s, 1H). MS 482.45 (M+H).

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc.

Preferred pharmaceutically acceptable salts are the hydrochlorides, trifluoroacetates and bitartrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

A) In Vitro Model

Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 100 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for $\mu$g protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2h in 0.1% polyethyleneimine. The radioactivity (dpm) retained on the filters was measured with a beta counter after soaking the filters for at least 12h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasable). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one-site model.

B) Biological Model (In Vivo Model)

Freund's Complete Adjuvant (FCA), And Sciatic Nerve Cuff Induced Mechano-Allodynia in Rat Animals Male Sprague-Dawley rats (Charles River, St-Constant, Canada) weighing 175–200 g at the time of surgery were used. They were housed in groups of three in rooms thermostatically maintained at 200° C. with a 12:12 hr light/dark cycle, and with free access to food and water. After arrival, the animals were allowed to acclimatize for at least 2 days before surgery. The experiments were approved by the appropriate Medical Ethical Committee for animal studies.

EXPERIMENTAL PROCEDURE

Freund's Complete Adjuvant

The rats were first anesthetized in a Halothane chamber after which 10 µl of FCA was injected s.c. into the dorsal region of the left foot, between the second and third external digits. The animals were then allowed to recover from anesthesia under observation in their home cage.

Sciatic Nerve Cuff

The animals were prepared according to the method described by Mosconi and Kruger (1996). Rats were anesthetized with a mixture of Ketamine/Xylazine i.p. (2ml/kg) and placed on their right side and an incision made over, and along the axis of, the lateral aspect of the left femur. The muscles of the upper quadriceps were teased apart to reveal the sciatic nerve on which a plastic cuff (PE-60 tubing, 2 mm long) was placed around. The wound was then closed in two layers with 3-0 vicryl and silk sutures.

Determination Of Mechano-Allodynia Using Von Frey Testing

Testing was performed between 08:00 and 16:00h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group and on post-operative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \text{ MPE} = \frac{\text{Drug treated threshold (g)} - \text{allodynia threshold (g)}}{\text{Control threshold (g)} - \text{allodynia threshold (g)}} \times 100$$

Administration Test Substance

Rats were injected (subcutaneously, intraperitoneally, or orally) with a test substance prior to von Frey testing, the time between administration of test compound and the von Frey test varied depending upon the nature of the test compound.

What is claimed is:

1. A compound according to formula I:

$$R^1\text{-N}(R^2)\text{-C(O)-N}(R^3)\text{-(CH}_2)_n\text{-[cyclohexyl]-(CH}_2)_m\text{-N}(R^4)(R^5) \quad (I)$$

wherein:
  m and n are each independently an integer from 1–3, and
    one or more of the hydrogens in the alkylene chain may optionally be substituted by any one of a $C_1$–$C_6$ alkyl; a $C_1$–$C_6$ alkoxy; or a hydroxy; or
one or more of the methylene groups may optionally be substituted by a heteroatom selected from O, N or S;

$R^1$ is selected from hydrogen; a branched or straight $C_1$–$C_6$ alkyl; a $C_2$–$C_6$ alkenyl; a $C_3$–$C_8$ cycloalkyl; a $C_4$–$C_8$(alkyl-cycloalkyl) wherein the alkyl is a $C_1$–$C_2$ alkyl and the cycloalkyl is a $C_3$–$C_6$ cycloalkyl;

$R^2$ is selected from any of:
  (i) hydrogen;
  (ii) a straight or branched $C_1$–$C_6$ alkyl; a $C_2$–$C_6$ alkenyl; or a $C_2$–$C_6$ alkynyl;
  (iii) a $((CH_2)_q$-aryl);
  (iv) a $((CH_2)_r$-heteroaryl) wherein the heteroaryl has from 5 to 10 atoms, each heteroatom being selected from any of S, N and O; and wherein the heteroaryl may optionally and independently be substituted by 1 or 2 substituents Y, wherein each Y is as defined below; and wherein q and r are each independently an integer from 0 to 3;
  (v) a $C_3$–$C_{10}$ cycloalkyl, optionally comprising one or more unsaturations and optionally substituted by one or more heteroaryls, wherein each heteroaryl has from 5 to 10 atoms and each heteroatom is selected from any of S, N and O; and wherein an aryl or heteroaryl may optionally and independently be substituted by 1 or 2 substituents Y, wherein each Y is as defined below;
  (vi) a heteroaryl having from 5 to 10 atoms, each heteroatom being selected from any of S, N and O; wherein the heteroaryl may optionally and independently be substituted by 1 or 2 substituents Y, wherein each Y is as defined below;
or $R^1$ and $R^2$ may optionally form a heterocyclic ring, which may optionally be saturated or unsaturated;

$R^3$ is selected from any one of:
  (i) hydrogen;
  (ii) a straight or branched $C^1$–$C_6$ alkyl; $C_2$–$C_6$ alkenyl; or $C_2$–$C_6$ alkynyl;
  (iii) a $C_6$–$C_{10}$ arylalkyl, wherein the aryl may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iv) a heteroaryl-($C_5$–$C_{10}$ alkyl), wherein the heteroaryl has from 5 to 10 atoms, each heteroatom being selected from any of S, N, O, and wherein the heteroaryl may optionally and independently be substituted by 1 or 2 substituents Y, wherein each Y is as defined below;
  (v) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein the aryl and heteroaryl may optionally and independently be substituted by 1 or 2 substituents Y, wherein each Y is as defined below;
  (vi) a ($C_3$–$C_6$ cycloalkyl-$(CH_2)_q$) wherein q is an integer from 1 to 3;

$R_4$ is selected from:
  (i) hydrogen;
  (ii) a straight or branched $C_1$–$C_6$ alkyl; $C_2$$C_6$ alkenyl; or $C_2$–$C_6$ alkynyl;
  (iii) a $C_6$–$C_{10}$ arylalkyl, wherein the aryl may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iv) a heteroaryl-($C_5$–$C_{10}$ alkyl), wherein the heteroaryl has from 5 to 10 atoms, each heteroatom being selected from any of S, N and O, and wherein the heteroaryl may optionally and independently be substituted by 1 or 2 substituents Y, wherein each Y is as defined below;
  (v) a $C_3$–$C_{10}$ cycloalkyl, optionally comprising one or more unsaturations and optionally substituted by one or more heteroaryls wherein each heteroaryl has from 5 to 10 atoms and each heteroatom is selected from any of S, N and O; and wherein an aryl or heteroaryl may optionally and independently be substituted by 1 or 2 substituents Y, wherein each Y is as defined below;
  (vi) a heteroaryl having from 5 to 10 atoms, each heteroatom being selected from any of S, N and O; wherein the heteroaryl may optionally and independently be substituted by 1 or 2 substituents Y, wherein each Y is as defined below;

$R^5$ is selected from any one of:
  (i) hydrogen;
  (ii) a straight or branched $C_1$–$C_6$ alkyl; $C_2$–$C_6$ alkenyl; or $C_2$–$C_6$ alkynyl;
  (iii) a $C_6$–$C_{10}$ arylalkyl, wherein the aryl may optionally be substituted by one or more heteroaryls having from 5 to 10 atoms, each heteroatom being selected from any of S, N and O; and wherein the aryl and heteroaryl may optionally and independently be substituted by 1 or 2 substituents Y, wherein each Y is as defined below;
  (iv) a heteroaryl-($C_5$–$C_{10}$ alkyl), wherein the heteroaryl has from 5 to 10 atoms, each heteroatom being selected from any S, N and O, and wherein the heteroaryl may optionally and independently be substituted by 1 or 2 substituents Y, wherein each Y is as defined below;
  (v) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein an aryl or heteroaryl may optionally and independently be substituted by 1 or 2 substituents Y, wherein each Y is as defined below;
  (vi) a heteroaryl having from 5 to 10 atoms, each heteroatom being selected from any of S, N and O, wherein the heteroaryl may optionally and independently be substituted by 1 or 2 substituents Y, wherein each Y is as defined below;

(vii)

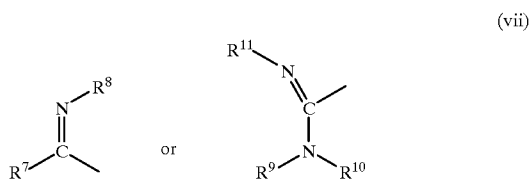

wherein $R^7$, $R^8$, $R^9$, $R^{10}$ and $R^{11}$ are each independently selected from:
  (a) hydrogen;
  (b) a straight or branched $C_1$–$C_6$ alkyl; $C_2$–$C_6$ alkenyl; or $C_2$–$C_6$ alkynyl;

(c) a $C_6$–$C_{10}$ arylalkyl, wherein the aryl may optionally be substituted by one or more heteroaryls having from 5 to 10 atoms, each heteroatom being selected from any of S, N and O, and wherein the aryl and heteroaryl may optionally and independently be substituted by 1 or 2 substituents Y, wherein each Y is as defined below;

(d) a heteroaryl-$C_5$–$C_{10}$ alkyl), wherein the heteroaryl has from 5 to 10 atoms, each heteroatom being selected from any of S, N and O, and wherein the heteroaryl may optionally and independently be substituted by 1 or 2 substituents Y, wherein each Y is as defined below;

(e) a $C_3$–$C_{10}$ cycloalkyl, optionally comprising one or more unsaturations and optionally substituted by one or more heteroaryls, each heteroaryl having from 5 to 10 atoms, and each heteroatom being selected from any of S, N and O; and wherein an aryl or heteroaryl may optionally and independently be substituted by 1 or 2 substituents Y, wherein each Y is as defined below;

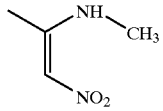

(viii)

or $R^4$ and $R^5$ may optionally form a heterocyclic ring, which may optionally be saturated or unsaturated;

Y is each and independently selected from any of $CH_3$; —$(CH_2)_{p1}CF_3$; halogen; $C_1$–$C_3$ alkoxy; hydroxy; —$NO_2$; —$OCF_3$; —$CONR^aR^b$; —$COOR^a$; —$COR^a$; —$(CH_2)_{p2}NR^aR^b$; —$(CH_2)_{p3}CH_3$; $(CH_2)_{p4}SOR^aR^b$; —$(CH_2)_{p6}SO_2R^a$; $(CH_2)_{p6}SO_2NR^a$; $C_4$–$C_8$(alkylcycloalkyl), wherein the alkyl is a $C_1$–$C_2$ alkyl and the cycloalkyl is a $C_3$–$C_6$ cycloalkyl; 1 or 2 heteroaryls having from 5 to 10 atoms, each heteroatom being selective from any of S, N and O; and oxides selected from N-oxides or sulfoxides; and wherein:

$R^a$ and $R^b$ are each independently selected from hydrogen; a branched or straight $C_1$–$C_6$ alkyl; a $C_1$–$C_6$ alkenyl; a $C_3$–$C_8$ cycloalkyl; and wherein p1, p2, p4, p5 are p6 are each and independently 0, 1 or 2; and p3 is 1 or 2;

as well as pharmaceutically acceptable salts of the compound of formula I and isomers, hydrates, isoforms and prodrugs thereof.

2. A compound according to formula I of claim 1, wherein:

m=n=1;

$R^1$ is selected from hydrogen and a $C_1$–$C_6$ alkyl;

$R^2$ is selected from:
  (i) hydrogen;
  (ii) a $C_6$–$C_{10}$ aryl, optionally and independently substituted by one or more heteroaryls having from 5 to 10 atoms, each heteroatom being selected from any of S, N and O, and wherein each heteroaryl may optionally and independently be substituted by 1 or 2 substituents Y, wherein each Y is as defined in claim 1;
  (iii) a $C_1$–$C_6$ alkyl; or
  (iv) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein an aryl or heteroaryl may optionally and independently be substituted by 1 or 2 substituents Y, wherein each Y is as defined in claim 1;

$R^3$ is selected from:
  (i) hydrogen;
  (ii) a $C_6$–$C_{10}$ arylalkyl, wherein the aryl may optionally be substituted by one or more heteroaryls having from 5 to 10 atoms, each heteroatom being selected from any of S, N and O, and wherein an aryl or heteroaryl may optionally and independently be substituted by 1 or 2 substituents Y, wherein each Y is as defined in claim 1;
  (iii) —($C_3$–$C_6$ cycloalkyl-$(CH_2)_q$) wherein q is an integer from 1 to 3;

$R^4$ is hydrogen;

$R^5$ is selected from any one of:
  (i) hydrogen;
  (ii) a straight or branched $C_1$–$C_6$ alkyl; $C_2$–$C_6$ alkenyl; or $C_2$–$C_6$ alkynyl;
  (iii) a $C_6$–$C_{10}$ arylalkyl, wherein the aryl may optionally be substituted by one or more heteroaryls having from 5 to 10 atoms, each heteroatom being selected from any of S, N and O; and wherein an aryl or heteroaryl may optional and independently be substituted 1 or 2 substituents Y, wherein each Y is as defined claim 1;
  (iv) a heteroaryl-($C_5$–$C_{10}$ alkyl), wherein the heteroaryl has from 5 to 10 atoms, each heteroatom being selected from any of S, N and O, and wherein the heteroaryl may optionally and independently be substituted 1 or 2 substituents Y, wherein each Y is as defined in claim 1;
  (v) a $C_3$–$C_{10}$ cycloalkyl, optionally comprising one or more unsaturations and optionally substituted by one or more heteroaryls having from 5 to 10 atoms, each heteroatom being selected from any of S, N and O, and wherein an aryl or heteroaryl may optionally and independently be substituted by 1 or 2 substituents Y, wherein each Y is as defined in claim 1;
  (vi) a heteroaryl having from 5 to 10 atoms, each heteroatom being selected from any of S, N and O, wherein the heteroaryl may optionally and independently be substituted by 1 or 2 substituents Y, wherein each Y is as defined in claim 1;

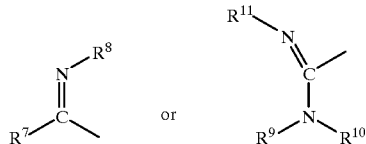

(vii)

wherein $R^7$, $R^8$, $R^9$, $R^{10}$, $R^{11}$ are each independently selected from:
  (a) hydrogen;
  (b) a straight or branched $C_1$–$C_6$ alkyl; $C_2$–$C_6$ alkenyl; or $C_2$–$C_6$ alkynyl;
  (c) a $C_6$–$C_{10}$ arylalkyl, wherein the aryl may optionally be substituted by one or more heteroaryls having from 5 to 10 atoms, each heteroatom being selected from any of S, N and O, and wherein an aryl or heteroaryl may optionally and independently be substituted by 1 or 2 substituents Y, wherein each Y is as defined in claim 1;
  (d) a heteroaryl-($C_5$–$C_{10}$ alkyl), wherein the heteroaryl has from 5 to 10 atoms, each heteroatom being selected from any of S, N and O, and wherein the heteroaryl may optionally and independently be substituted by 1 or 2 substituents Y, wherein each Y is as defined in claim 1;

(e) a $C_3$–$C_{10}$ cycloalkyl, optionally comprising one or more unsaturations and optionally substituted by one or more heteroaryls, each heteroaryl having from 5 to 10 atoms, each heteroatom being selected from any of S, N and O, and wherein an aryl or heteroaryl may optionally and independently be substituted by 1 or 2 substituents Y, wherein each Y is as defined in claim 1;

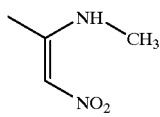

(viii)

or $R_4$ and $R_5$ may optionally form a heterocyclic ring, which may optionally be saturated or unsaturated.

3. A compound according to claim 1, which compound is any one selected from 2.

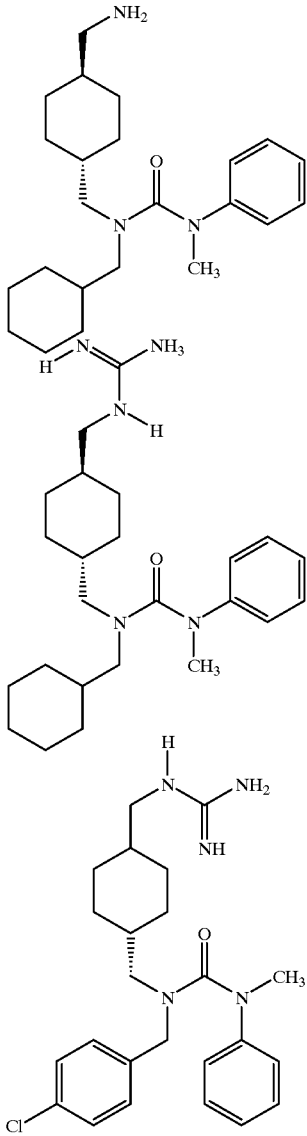

-continued

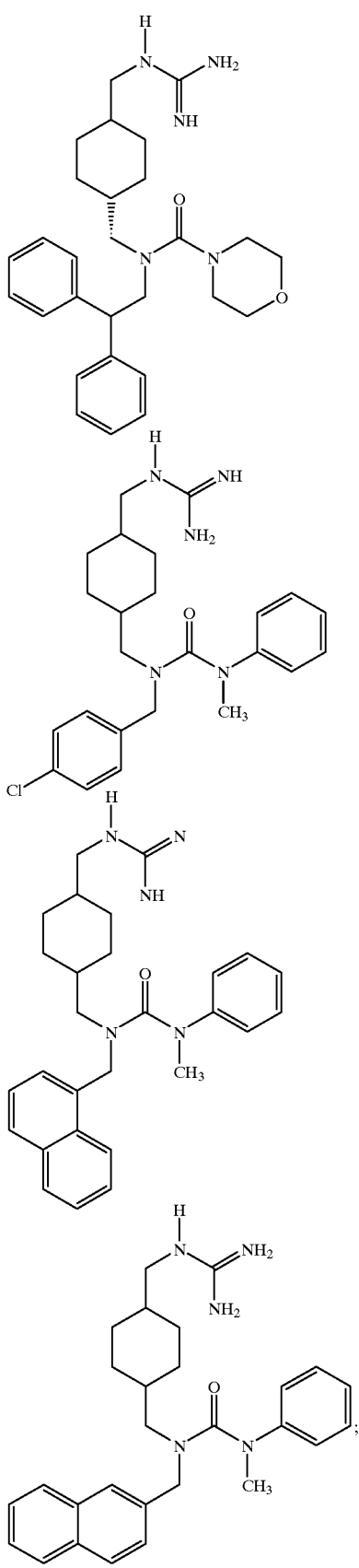

-continued

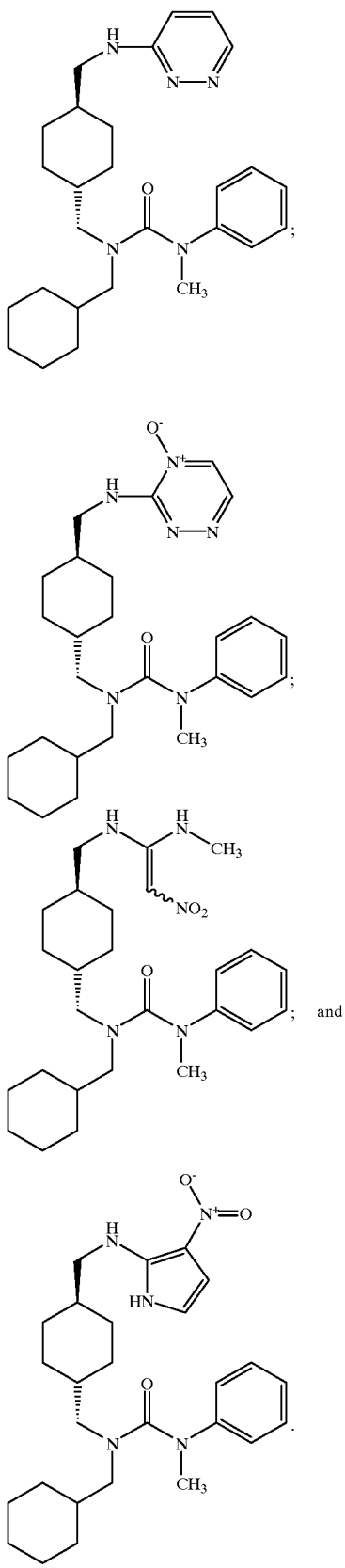

4. A compound according to any one of claim 3, 1, or 2 wherein said compound is in the form of a hydrochloride, sulfate, tartrate or citrate salt.

5. A compound according to any one of claim 3, 1, or 2, wherein said compound is isotopically labeled.

6. A compound of the formula (D)

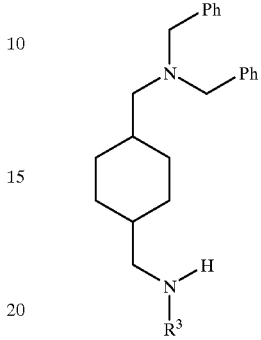

(D)

wherein

R$^3$ is selected from any one of
(i) hydrogen
(ii) a straight or branched C$_1$–C$_6$ alkyl, C$_2$–C$_6$ alkenyl or C$_2$–C$_6$ alkynyl;
(iii) C$_6$–C$_{10}$ arylalkyl, wherein the aryl may optionally be substituted by one or more heteroaryls having from 5 to 10 atoms and the heteroatom is selected from any of S, N and O; and wherein the aryl and heteroaryl may optionally and independently be substituted by 1 or 2 substituents Y;
(iv) heteroaryl-(C$_5$–C$_{10}$alkyl), where the heteroaryl has from 5 to 10 atoms and the heteroatom is selected from any of S, N and O, and wherein the heteroaryl may optionally and independently be substituted by 1 or 2 substituents Y;
(v) C$_3$–C$_{10}$ cycloalkyl optionally comprising one or more unsaturations and optionally substituted by one or more heteroaryls having from 5 to 10 atoms and the heteroatom is selected from any of S, N and O, and wherein the aryl and heteroaryl may optionally and independently be substituted by 1 or 2 substituents Y;
(vi) ((C$_3$–C$_6$ cycloalkyl)-(CH$_2$)$_q$) where q is an integer of from 1 to 3; and Y is each and independently selected from any of CH$_3$; —(CH$_2$)$_{p1}$ CF$_3$; halogen; C$_{1-C3}$ alkoxy; hydroxy; —NO2; —OCF$_3$; —CONR$^a$R$^b$; —COOR$^a$; —COR$^a$; —(CH$_2$)$_{p2}$NR$^a$R$^b$; —(CH$_2$)$_{p3}$CH$_3$; (CH$_2$)$_{p4}$SOR$^a$R$^b$; —(CH$_2$)$_{p5}$SO$_2$R$^a$; —(CH$_2$)$_{p6}$SO$_2$NR$^a$; C$_4$–C$_8$(alkylcycloalkyl), wherein the alkyl is a C$_1$–C$_2$ alkyl and the cycloalkyl is a C$_3$–C$_6$ cycloalkyl; 1 or 2 heteroaryls having from 5 to 10 atoms, each heteroatom being selective from any of S, N and O; and oxides selected from N-oxides or sulfoxides; and wherein R$^a$ and R$^b$ are each independently selected from hydrogen; a branched or straight C$_1$–C$_6$ alkyl; a C$_1$–C$_6$ alkenyl; a C$_3$–C$_8$ cycloalkyl; and wherein p1, p2, p4, p5 are p6 are each and independently 0, 1 or 2; and p3 is 1 or 2.

7. A compound of the formula (F)

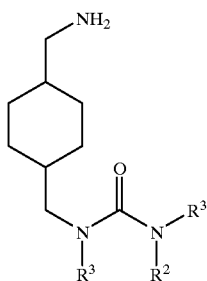

(F)

wherein
R¹ is selected from hydrogen, a branched or straight $C_1$–$C_6$ alkyl, $C_1$–$C_6$ alkenyl, $C_3$–$C_8$ cycloalkyl, $C_4$–$C_8$ (alkyl-cycloalkyl) wherein the alkyl is $C_{1-2}$ alkyl and the cycloalkyl is $C_3$–$C_6$ cycloalkyl;
R² is selected from any of
  (i) hydrogen;
  (ii) a straight or branched $C_1$–$C_6$ alkyl, $C_2$–$C_6$ alkenyl or $C_2$–$C_6$ alkynyl;
  (iii) —$(CH_2)_q$-aryl;
  (iv) —$(CH_2)_r$-heteroaryl) where the heteroaryl has from 5 to 10 atoms and the heteroatom is selected from any of S, N and O; and wherein the heteroaryl may optionally and independently be substituted by 1 or 2 substituents Y where each Y is as defined in claim 1; and wherein q and r is each and independently an integer from 0 to 3;
  (v) $C_3$–$C_{10}$ cycloalkyl, optionally comprising one or more unsaturations and optionally substituted by one or more heteroaryls where the heteroaryl has from 5 to 10 atoms and the heteroatom is selected from any of S, N and O; and wherein the heteroaryl may optionally and independently be substituted by 1 or 2 substituents Y where each Y is as defined in claim 1;
  (vi) heteroaryl having from 5 to 10 atoms, the heteroatom being selected from any of S, N and O; wherein the heteroaryl may optionally and independently be substituted by 1 or 2 substituents Y wherein each Y is as defined in claim 1;
  or
R¹ and R² may optionally form a heterocyclic ring;
R³ is selected from any one of
  (i) hydrogen;
  (ii) a straight or branched $C_1$–$C_6$ alkyl, $C_2$–$C_6$ alkenyl or $C_2$–$C_6$ alkynyl;
  (iii) $C_6$–$C_{10}$ arylalkyl, wherein the aryl may optionally be substituted by one or more heteroaryls having from 5 to 10 atoms and the heteroatom is selected from any of S, N and O; and wherein the aryl or heteroaryl may optionally and independently be substituted by 1 or 2 substituents Y wherein each Y is as defined in claim 1;
  (iv) heteroaryl-($C_5$–$C_{10}$ alkyl), where the heteroaryl has from 5 to 10 atoms and the heteroatom is selected from any of S, N and O, and wherein the heteroaryl may optionally and independently be substituted by 1 or 2 substituents Y where each Y is as defined in claim 1;
  (v) $C_3$–$C_{10}$ cycloalkyl, optionally comprising one or more unsaturations and optionally substituted by one or more heteroaryls having from 5 to 10 atoms and the heteroatom is selected from any of S, N and O, and wherein the aryl or heteroaryl may optionally and independently be substituted by 1 or 2 substituents Y where each Y is as defined in claim 1;
  (vi) —($C_3$–$C_6$ cycloalkyl)-$(CH_2)_q$) where q is an integer of from 1 to 3.

8. A method for the treatment of a patient for pain, comprising administering to said patient an effective amount of a compound of the formula I according to claim 1.

9. A method for the treatment of a patient for a gastrointestinal disorder, comprising administering to said patient an effective amount of a compound of formula I according to claim 1.

10. A method for the treatment of a patient for a spinal injury, comprising administering to said patient an effective amount of a compound of formula I according to claim 1.

11. A compound according to either claim 1 or claim 2, wherein:
m=n=1;
R¹ is selected from:
  (i) hydrogen; and
  (ii) methyl;
R² is selected from:
  (i) hydrogen;
  (ii) phenyl;
  (iii) a $C_1$–$C_3$ alkyl;
  (iv) $C_3$–$C_6$ cycloalkyl;
or R¹ and R² together form a ring of from 4 to 6 atoms selected from C, N and O;
R³ is selected from:
  (i) hydrogen;
  (ii) —$CH_2$-cyclohexyl;
  (iii) —$CH_2$-phenyl, optionally substituted by one or two halogens;
  (iv) —$CH_2$-naphthyl;
R⁴ is hydrogen;
R⁵ is selected from:
  (i) hydrogen;

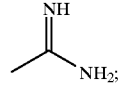

(ii)

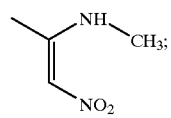

(iii)

(iv) a heteroaryl having from 5 to 10 atoms, each heteroatom being selected from any of S, N and O, wherein the heteroaryl may optionally and independently be substituted by 1 or 2 substituents, Y, wherein each Y is as defined in claim 1.

12. A method of diagnosing a disease characterized by the degeneration or dysfunction of opioid receptors, comprising administering to a subject an effective amount of the isotopically labeled compound of claim 5.

13. A process for the preparation of a compound of formula I according to claim 1, comprising:
(a) protecting an amine of formula (A):

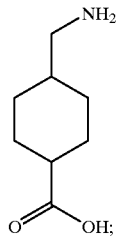

(A)

(b) subjecting the protected compound of step (a) to amidation to produce a compound of formula (C):

(C)
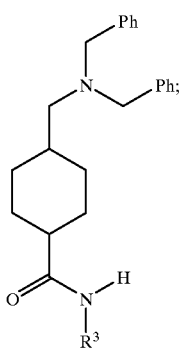

(c) reducing said compound of formula (C);
(d) reacting the product of step (c) with a dialkylcarbamoyl chloride, to produce a compound of formula (E):

(E)
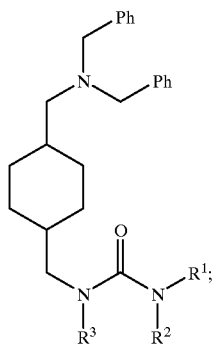

(e) deprotecting the N,N-dibenzyl group in said compound of formula (E);
(f) guanylating, amidating or alkylating the compound of step (e) to produce a compound of formula (G):

(G)
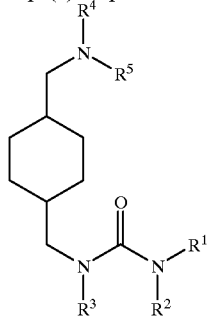

wherein
$R^1$, $R^2$, $R^3$, $R^4$, and $R^5$ in formulas (A), (C), (E), and (G) are as defined in formula I of claim 1.

14. A process for the preparation of a compound of formula I according to claim 11, comprising:
(a) converting a cis/trans-mixture of 1,4-bis-aminomethyl cyclohexane into a mono-(di-Boc)-guanidinomethyl derivative using a protected guanylating reagent;
(b) reductively aminating the product of step (a);
(c) treating the product of step (b) with an aldehyde, $R^3$CHO, to produce a compound of formula (L):

(L)
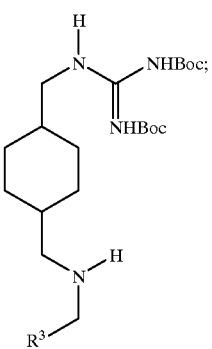

(d) reacting said compound of formula (L) with a dialkylcarbamoylchloride in the presence of a tertiary amine to produce a compound of formula (M):

(M)
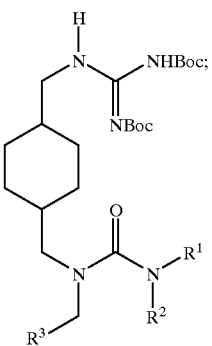

(e) deprotecting the Boc-protecting groups in said compound of formula (M) to produce a cis,trans-guanidinomethyl cyclohexane compound of formula (N):

(N)
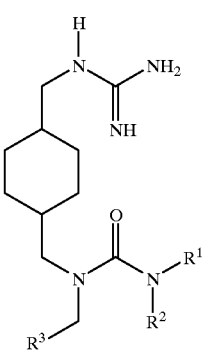

wherein
$R^1$, $R^2$, and $R^3$ in formulas (L), (M) and (N) are as defined in formula I of claim 1.

15. A pharmaceutical composition comprising a compound of the formula I according to claim 1 as an active ingredient, together with a pharmacologically and pharmaceutically acceptable carrier.

* * * * *